(12) United States Patent
Hilgers et al.

(10) Patent No.: US 6,702,791 B1
(45) Date of Patent: *Mar. 9, 2004

(54) NEEDLE FOR BODY FLUID TESTER

(75) Inventors: Michael Edward Hilgers, Roseville, MN (US); Bruno J. Schmidt, Moundsview, MN (US)

(73) Assignee: Integ, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,161

(22) Filed: Oct. 26, 1999

Related U.S. Application Data

(63) Continuation-in-part of application No. 09/244,952, filed on Feb. 4, 1999, now abandoned.

(51) Int. Cl.⁷ .................................................. A61M 5/32
(52) U.S. Cl. .................................. 604/274; 604/239
(58) Field of Search .............................. 604/181, 187, 604/239, 264, 272, 274, 411, 506

(56) References Cited

U.S. PATENT DOCUMENTS

| | | |
|---|---|---|
| 3,872,806 A | 3/1975 | Bone |
| 3,906,932 A | 9/1975 | Ayres |
| 3,924,617 A * | 12/1975 | Ferro .......................... 604/411 |
| 4,368,738 A | 1/1983 | Tersteegen et al. |
| 4,383,530 A * | 5/1983 | Bruno ......................... 604/274 |
| 4,518,383 A | 5/1985 | Evans |
| 4,753,641 A | 6/1988 | Vaslow |
| 4,799,494 A * | 1/1989 | Wang .......................... 600/566 |
| 4,808,170 A | 2/1989 | Thornton et al. |
| 4,889,529 A * | 12/1989 | Haindl ........................ 604/274 |
| 5,295,980 A | 3/1994 | Ersek |
| 5,403,296 A | 4/1995 | Mohring et al. |
| 5,505,694 A * | 4/1996 | Hubbard et al. ............. 604/512 |
| 5,601,475 A | 2/1997 | Stametz et al. |
| 5,607,401 A * | 3/1997 | Humphrey ................... 604/239 |
| 5,810,788 A | 9/1998 | Racz |
| 5,820,570 A | 10/1998 | Erickson et al. |
| 5,823,973 A | 10/1998 | Racchini et al. |
| 2003/0060784 A1 | 3/2003 | Hilgers et al. |

FOREIGN PATENT DOCUMENTS

| | | |
|---|---|---|
| EP | 0 872 215 A2 | 10/1998 |
| WO | WO 82/02678 | 8/1982 |

* cited by examiner

Primary Examiner—Brian L. Casler
Assistant Examiner—Michael M Thompson
(74) Attorney, Agent, or Firm—Carol M. LaSalle; Bozicevic, Field & Francis, LLP

(57) ABSTRACT

An apparatus for collecting a body fluid for testing for an analyte includes a needle for penetrating a patient's skin to access the fluid within the skin. The needle has a hollow body extending from a first end to a second end. An interior surface of the body defines a fluid pathway extending between the ends. The second end is positioned to deposit fluid for testing. The first end has a beveled face on a front side of the body. The beveled face terminates at a penetration tip with the beveled face having an opening in communication with the fluid pathway. The penetration tip is burnished to a rounded shape and bent to facilitate low pain and rapid fluid collection.

10 Claims, 7 Drawing Sheets

US 6,702,791 B1

NEEDLE FOR BODY FLUID TESTER

CROSS-REFERENCE TO RELATED APPLICATION

The present application is a continuation-in-part of U.S. patent application Ser. No. 09/244,952 filed Feb. 4, 1999, now abandoned the disclosure of which is hereby incorporated by reference.

TECHNICAL FIELD

This invention pertains to testing a body fluid for an analyte. More specifically, the present invention pertains to a novel needle design in combination with a collection apparatus for collecting a sample of such a fluid.

BACKGROUND

Numerous patents teach various ways for collecting a sample of body fluid and testing such fluid for an analyte such as glucose. For example, U.S. Pat. Nos. 5,820,570 and 5,823,973 describe methods and apparatus for obtaining, in one embodiment, interstitial fluid which is tested for glucose through IR absorption. These patents also describe use of the disclosed inventions in colormetric and electro-chemical testing of glucose.

Present development efforts are directed to testing very small volumes of body fluid (e.g. about 0.5 $\mu$l). The use of such small volumes of fluid permits less painful collection of a fluid samples. However, small fluid volumes present additional challenges for analyte testing. For example, testing for analytes typically requires a fluid sample in excess of a predetermined minimum volume. By way of non-limiting representative example, a test may require a minimum sample size of about 1 to 5 $\mu$l to yield reliable test results.

The '973 patent shows a small diameter needle (about 28 to 32 gauge or about 0.36 mm to 0.23 mm outside diameter) with a length to penetrate into but not through a dermis to access interstitial fluid contained within the dermis. Preferably, the fluid is blood-free to facilitate subsequent testing of the fluid for analytes such as glucose.

The use of a small needle dimensioned as described in the '973 patent greatly reduces pain. However, pain may occasionally occur. Further, there is a need for a needle design that enhances the rate at which a sample is collected by such a needle.

SUMMARY

The present invention is directed to an apparatus for collecting a body fluid for testing for an analyte contained within said body fluid. The apparatus comprises a needle for penetrating a patient's skin to access the fluid within said skin. The needle has a hollow body extending from a first end to a second end with a fluid pathway extending between the ends. The second end is positioned to deposit fluid for testing. The first end is configured to penetrate the skin and includes a beveled face on a front side of said body. The beveled face terminates at a penetration tip. The beveled face has an opening in communication with the fluid pathway. The body has a linear axis adjacent the first end. The first end includes a bend formed on the front side of the beveled face to be deflected toward said front side.

DETAILED DESCRIPTION

Figure 1:
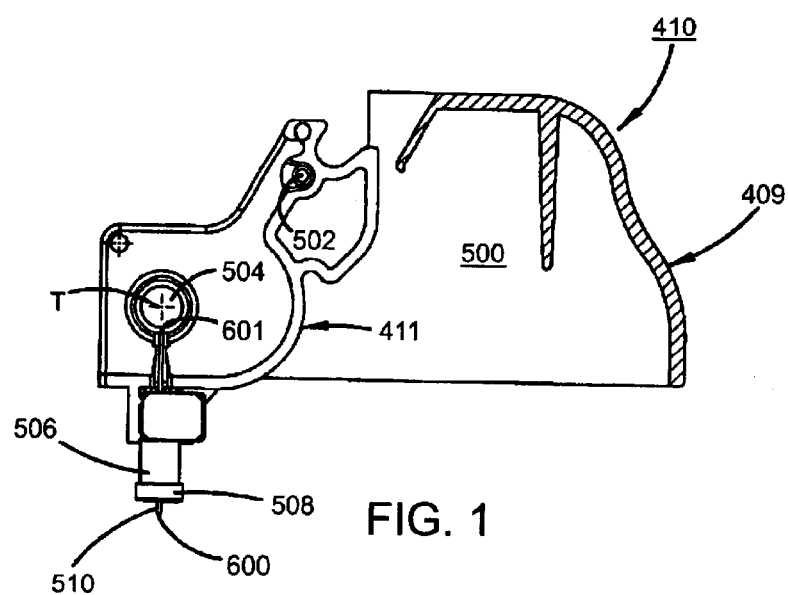
FIG. 1 is a side elevation view of a needle contained in a sampler.

Various embodiments of the present invention, including a preferred embodiment, will be described in detail with reference to the drawings wherein like reference numerals represent like parts and assemblies throughout the several views. Reference to the described embodiments does not limit the scope of the invention, which is limited only by the scope of the appended claims.

Throughout the following description, an embodiment of the present invention will be described with reference to collecting a sample of interstitial fluid for glucose testing using a narrow needle that penetrates into, but not through, the dermis. Such sample collection is more fully described in commonly assigned U.S. Pat. Nos. 5,823,973 and 5,820,570, the disclosures for both of which are hereby incorporated by reference as though set forth in full. While such a use is a preferred embodiment, the present invention is applicable to other fluid collection systems as well as testing for other fluid analytes.

Figure 2:
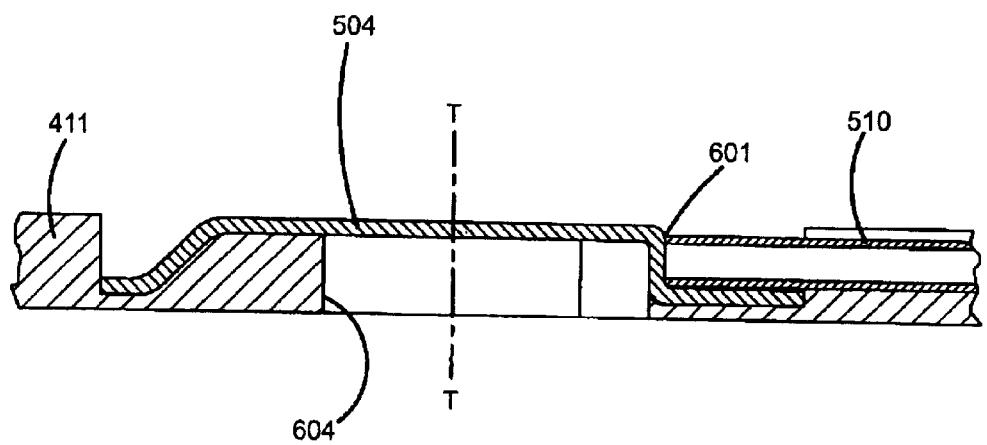
FIG. 2 is a side sectional view of a needle positioned relative to an absorbent membrane.

FIG. 1 illustrates a fluid sampler 410 such as that shown in FIGS. 36–40 of U.S. Pat. No. 5,823,973 (the '973 patent), the disclosure of which is hereby incorporated herein by reference. FIG. 2 illustrates a membrane and needle assembly such as that shown in FIG. 43 of the '973 patent. For ease of illustration, the present invention will be described to a needle alignment such as that shown in the '973 patent with the axis of the needle parallel to the surface of an absorbing membrane. The invention could also be used in other arrangements. For example, the needle axis can be perpendicular to the membrane and fluid can flow through the membrane to an opposite side for colormetric testing.

Referring now to FIGS. 1 and 2, the sampler 410 has a hollow handle end 409 with an interior 500 to receive a sample end 411. The sample end 411 pivots on a pin 502. The sample end 411 then can pivot between a storage position within the hollow handle end 409 and a deployed position. FIG. 1 shows the sample end 411 pivoted into the deployed position.

The sample end 411 is configured to receive samples such as a fluid. An absorbent membrane 504 is carried on the sample end 411. The sample end 411 also includes a hub or ferrule 506 that terminates at a ring end 508. In one possible embodiment, the ring end may serve as a pressure ring. A needle 510 is held by the ferrule 506. Additionally, the sample end 411 defines a hole 604 (FIG. 2). An absorbent membrane 504 has a target area T and is arranged so that the target area T overlies the hole 604.

Figure 3:
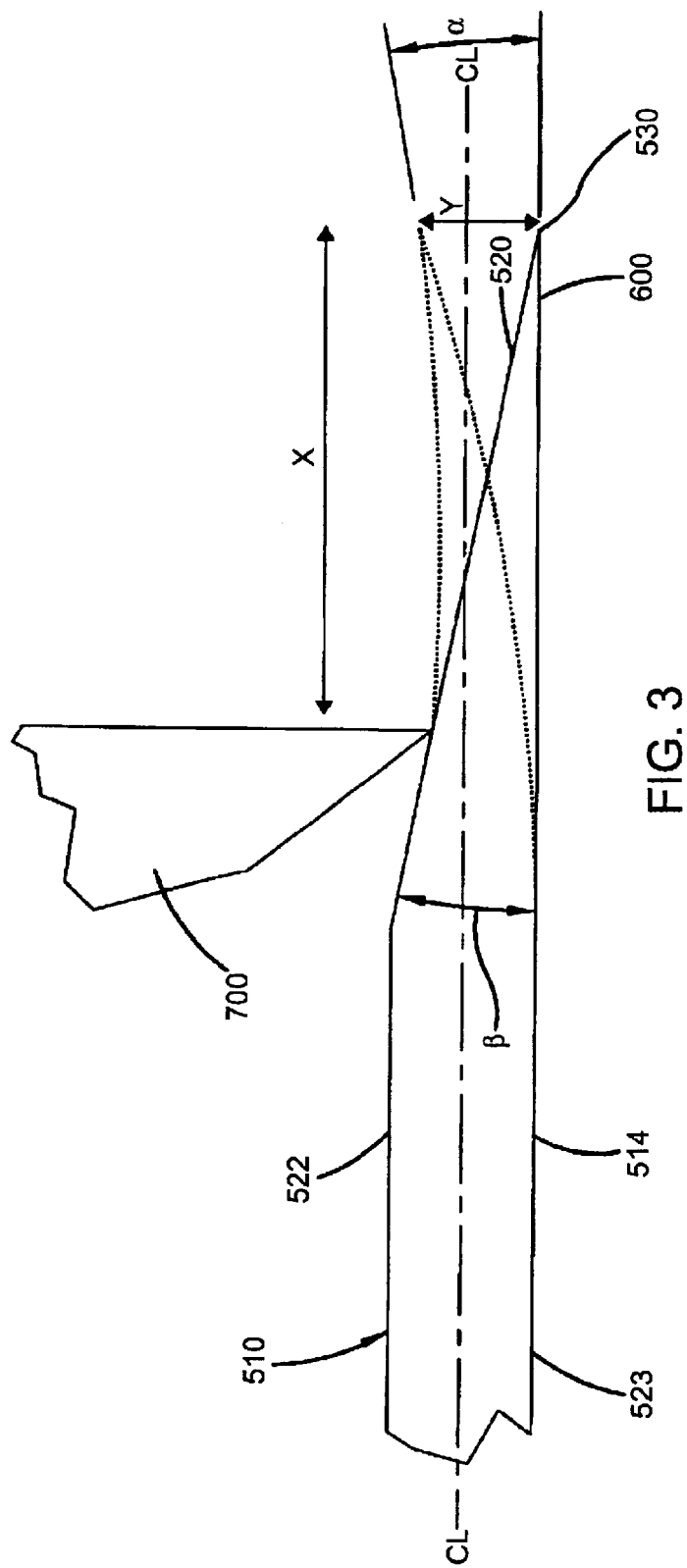
FIG. 3 is a side elevation view of a needle being bent.

As shown in FIG. 3, the needle 510 includes a hollow, straight tubular body 514, a first or penetration end 600, and a discharge end 601 (shown in FIGS. 1 and 2). In one embodiment, the needle 510 is a 30 gauge needle, about 0.3 mm in outside diameter, although other needle gauges can be used. In a preferred embodiment, the penetration end 600 protrudes from the ring end 508 of the ferrule by a predetermined distance. The predetermined distance is set so that the first end 600 will penetrate into, but not through, a patient's dermis when the ring 508 is placed against his or her skin.

The discharge end 601 abuts an absorbent membrane 504 mounted on the sample end 411. In this configuration, the longitudinal axis of the needle 510 is perpendicular to the portion of the membrane 504 that forms the target area T. Additionally, the tubular body 514 has an interior surface 511 (FIG. 5) that defines a fluid pathway 512 extending completely through the needle body 514.

In use, the penetration end 600 of the needle 510 is inserted into the patient's dermis. Fluid then flows along the fluid pathway 512 and through the absorbent membrane 504 to the target area T. The absorbent membrane 504 filters out undesirable stray blood cells that may be present in the fluid. The fluid at the target area can then be tested for elements such as glucose.

One possible way to test the fluid is through the use of infrared light. Alternative embodiments include but are not limited to depositing the fluid on a test strip for colormetric testing or on electrodes for electro-chemical testing.

Figure 4:
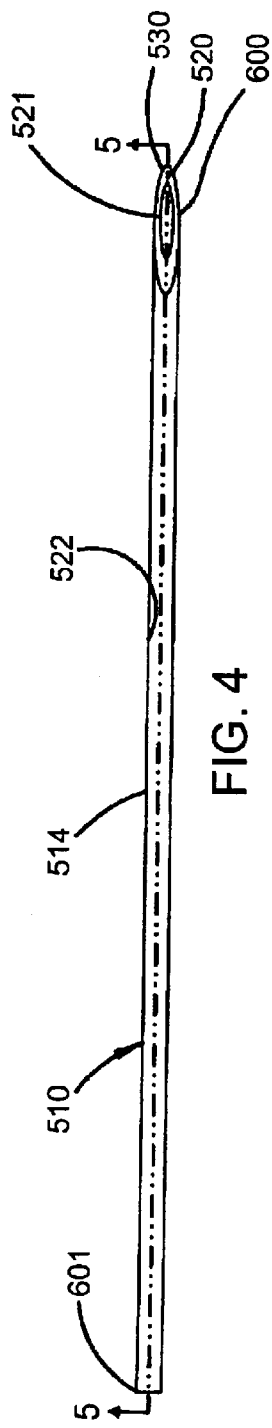
FIG. 4 is a top plan view of a bent needle.
Figure 5:
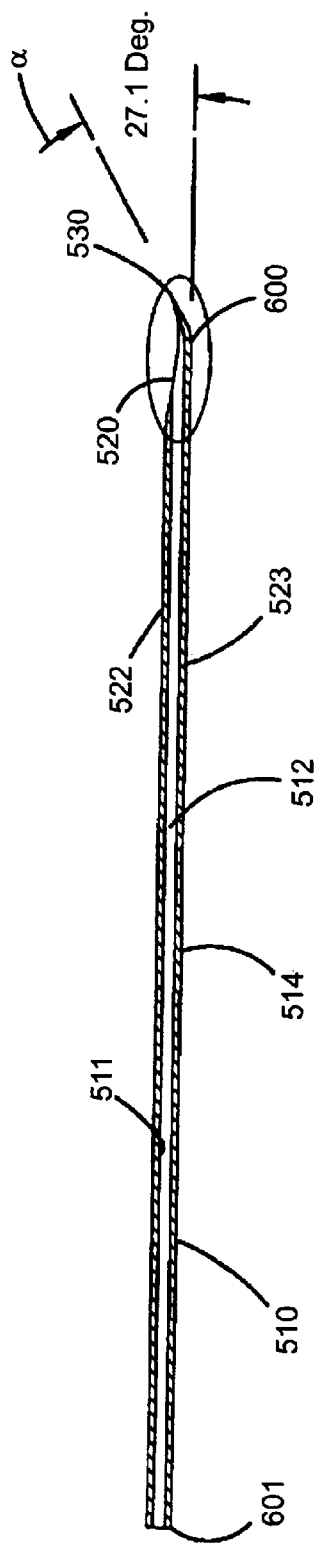
FIG. 5 is a view taken along line 5—5 of FIG. 4.

Referring to FIGS. 4 and 5, the needle 510 has a primary beveled face 520 and tip 530 formed at its penetration end 600. An entrance hole 521 is formed in the beveled face 520 and is in fluid communication with the fluid path 512. The needle 510 also has a front side 522 and an opposite back side 523. The tip 530 of the needle 510 is displaced toward the front side 522 of the needle 510.

Referring to FIG. 3, one possible way to form the needle 510 is as follows. The penetration end 600 of the hollow body 514 is ground at an angle to define the beveled face 520 so that it extends through the body 514 and forms the sharp penetration tip 530. In one possible embodiment, the beveled face is formed at an angle β (about 9°) with respect to a longitudinal axis CL—CL of the needle body 514. The formation of a beveled face 520 results in formation of the entrance hole 521 on beveled face 520. The present invention is shown with a needle having a single grind forming the beveled face. The present invention is also applicable to needles with multiple grinds forming the beveled face.

After providing a needle body 514 with a flat beveled face 520, a fulcrum 700 is placed at a bend location, which is a distance X from the tip 530. In one possible embodiment, the distance X is about 1.2 mm, although other distances can be used. The tip 530 is then urged toward the front side 522 to permanently displace the tip 530 and form a bend angle α. When the tip 530 is displaced, it moves from being aligned with a plane of the back side 523 of the body 514 to a location spaced by a distance Y from the plane of the back side 523. This method creates an arcuate bend which is approximated in the Figures by the bend angle α. In one possible embodiment, the bend angle α is about 27.1°, although other bend angles are possible.

For reasons not fully understood, the use of a displaced tip 530 results in enhanced fluid collection. Possibly, a pocket is formed around the opening 521 to improve fluid flow. Whatever the mechanism, fluid collection is enhanced. Further, the degree of enhancement improves with the amount of deflection Y. The following table illustrates the amount of time required to collect an adequate sample (in the test presumed to be about 0.9 μl of fluid) for an average of needle samples at various tip displacements Y and for a variety of axial locations X (with X and Y as defined with reference to FIG. 3). The amount of time greatly decreases with an increase in Y. In fact, displacement of the tip above the front plane of the needle body has resulted in enhanced collection. In the following table, negative values of a and Y reflect a backward bending of the tip behind the rear side of the needle. Zero values reflect an unbent needle.

TABLE A

Time to Collect Pre-determined Amount of Sample

| Location X (mm) | Angle α (degrees) | Displacement Y (mm) | Time to Collect .9 μl of Sample (seconds) |
|---|---|---|---|
| 1.07 | −6.03 | −0.14 | 26.75 |
| 0 | 0 | 0 | 15.51 |
| 0.88 | 3.24 | 0.09 | 12.75 |
| 1.57 | 5.71 | 0.13 | 10.41 |
| 0.86 | 11.3 | 0.15 | 11.46 |
| 2.03 | 8.13 | 0.25 | 12.74 |
| 1.30 | 12.8 | 0.279 | 9.04 |
| 0.59 | 28.3 | 0.281 | 7.63 |
| 1.68 | 13.7 | 0.38 | 7.96 |
| 0.94 | 25.9 | 0.43 | 6.62 |
| 1.41 | 21.6 | 0.51 | 5.66 |

Figure 5B:
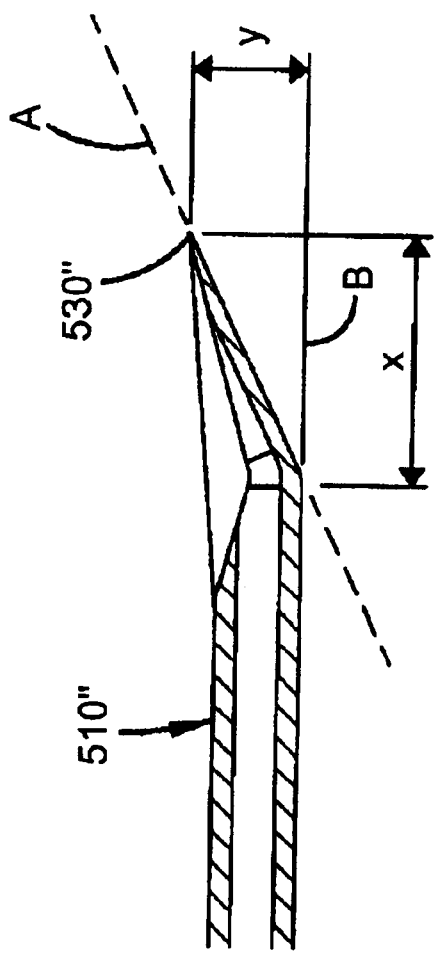
FIG. 5B is a view taken along lines 5B—5B of FIG. 5A and providing an enlarged view of a bent tip of the needle of FIG. 5 and showing a preferred embodiment with the tip bent above the needle.
Figure 5A:
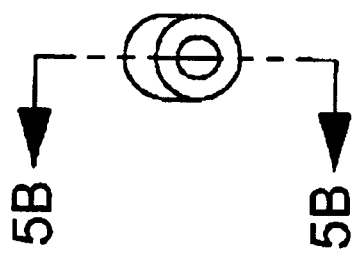
FIG. 5A is an end view of a discharge end of a bent needle.

FIGS. 5A and 5B illustrate a preferred embodiment where the tip 530" is displaced above the front side 522" of the needle 510". In FIGS. 5A and 5B, elements in common with those of the embodiment of FIGS. 3–5 are similarly numbered (and need not be separately discussed beyond what follows) with the addition of a double apostrophe to distinguish the embodiments.

The needle 510" is 0.012 inch (about 0.3048 mm or 30 gauge) outside diameter.

The preferred embodiment was derived following experimentation subsequent to that enumerated in the above table. In FIG. 5B, the bend angle θ is the lesser included angle of a straight line A tangent to the bent portion 600" and an extension line B of the straight portion. The distance Y is the distance between the tip 530" and the straight line extension B. The distance X is the distance from the intersection of the tangent line A and straight line extension B to the tip 530". All of the data in the following table illustrate fluid collection rate (measured in micro-liters per second, μl/sec.) as measured using a preferred value of X equal to 0.035 inch (about 0.8890 mm). The negative values for θ and Y represent a downward bend. Positive values represent upward bends as illustrated in FIG. 5B. A zero value represents an unbent needle.

TABLE B

Fluid Collection Rate (Micro-Liters/Second)

| Bend Angle (θ) in degrees | VALUES of Y | | | | | |
|---|---|---|---|---|---|---|
| | −.006 inch (≈−.1524 mm) | .000 inch (≈.0000 mm) | .005 inch (≈.1270 mm) | .012 inch (≈.3048 mm) | .016 inch (≈.4064 mm) | .020 inch (≈.5080 mm) |
| −8.1 | 0.06 | | | | | |
| 0.0 | | 0.10 | | | | |
| 4.6 | | | 0.13 | | | |
| 6.5 | | | 0.13 | | | |
| 7.1 | | | | 0.12 | | |
| 7.6 | | 0.10 | | | | |
| 10.0 | | 0.14 | | | | |
| 12.2 | | | | 0.15 | | |
| 12.2 | | | | 0.13 | | |
| 12.8 | | | | | 0.16 | |
| 14.9 | | | | 0.13 | | |
| 16.8 | | | | 0.13 | | |
| 20.0 | | | | | | 0.19 |
| 21.6 | | | | | | 0.17 |
| 21.8 | | | | 0.16 | | |
| 24.7 | | | | | 0.19 | |
| 25.6 | | | | 0.18 | | |
| 26.6 | | | | 0.15 | | |
| 31.2 | | | | | | 0.20 |
| 46.4 | | | | | | 0.20 |

Figure 9:
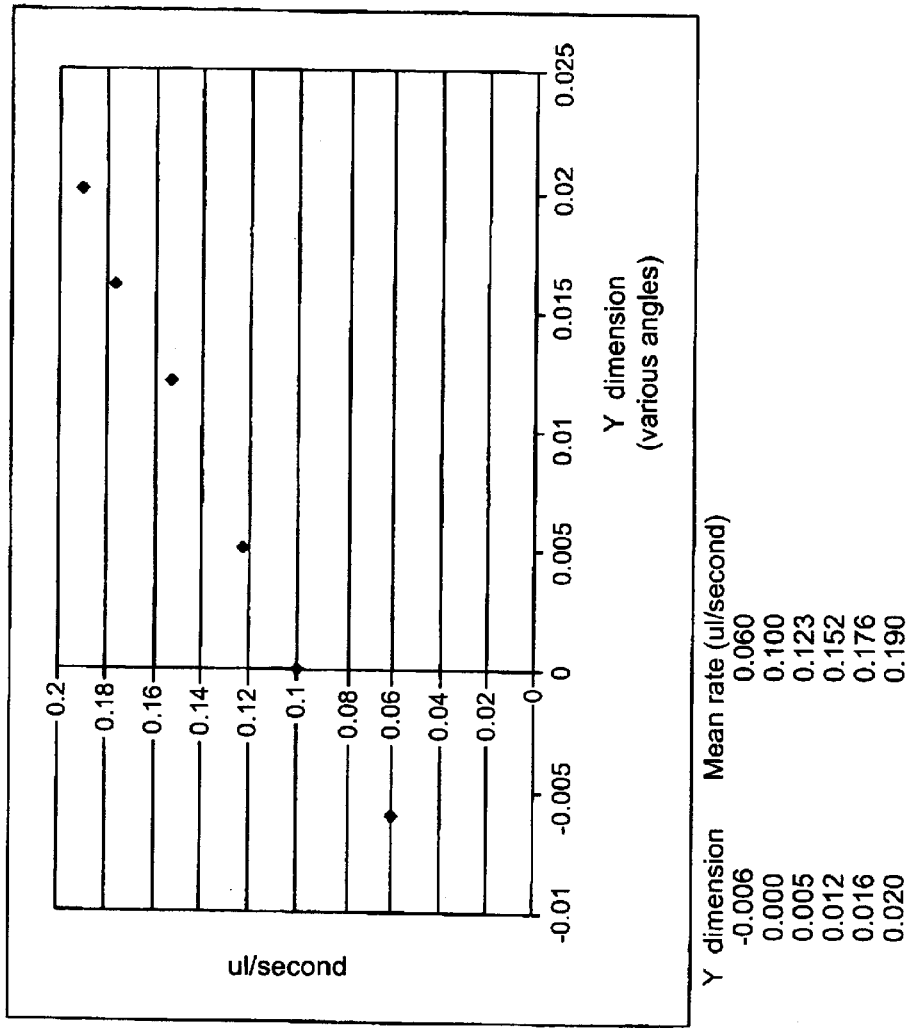
FIG. 9 is a graphical representation of a collection rate as a finction of needle tip displacement for a needle such as that shown in FIGS. 5A and 5B.
Figure 10:
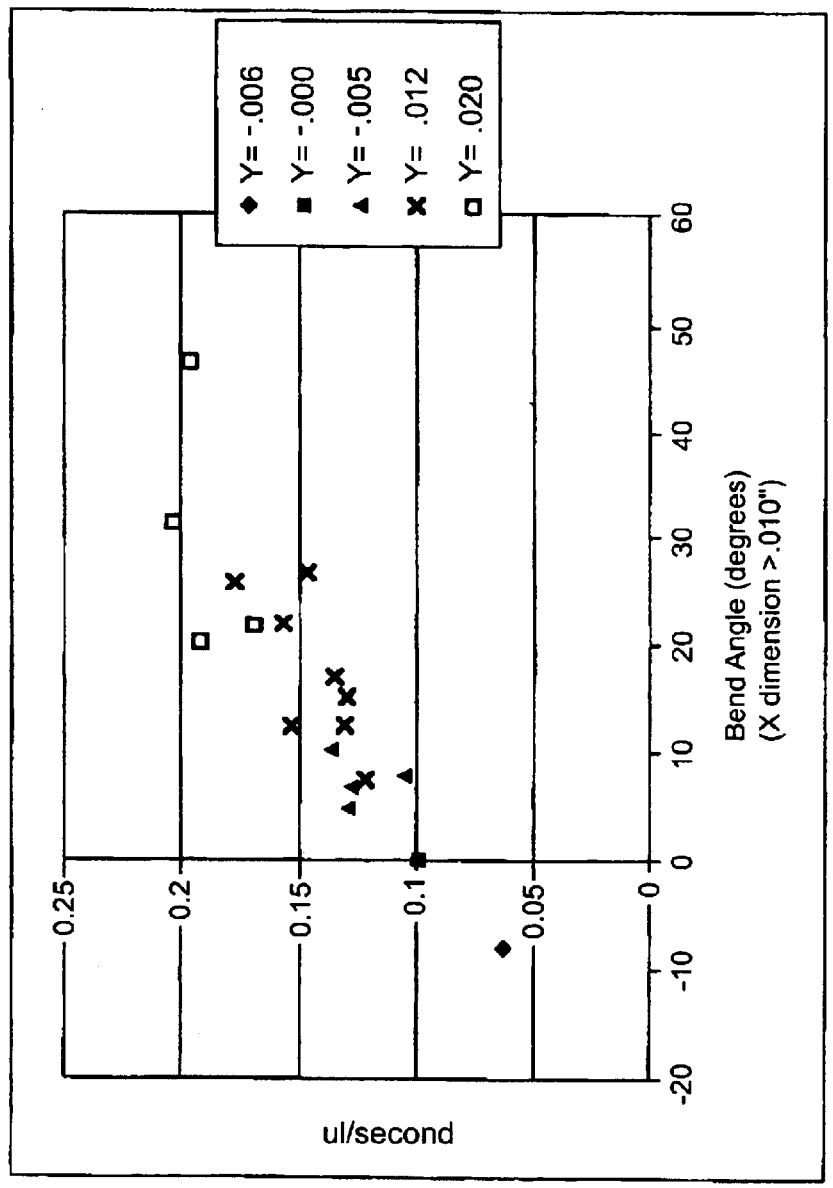
FIG. 10 is a scatter chart of a collection rate as a function of the bend angle of a needle tip for a needle such as that shown in FIGS. 5A and 5B.

Using the above data, FIG. 9 is a graphical representation of the collection rate (μl/sec.) as a function of the Y displacement (where Y is the average Y values for various angles from the data in FIG. θ). FIG. 10 is a scatter chart of the data plotted as collection rate (μl/sec.) as a function of the bend angle θ.

The above data show for a small gauge needle, collection rate improves with increases in both the bend angle θ and the displacement Y. In fact, displacements greater than the needle's outside diameter of 0.012 inch (representing a bending of the tip 530" above the front side 522" of the needle 510") shows improved collection rates.

Since pain avoidance is a desirable feature, patients selected to collect the above data were asked to compare pain sensation using the above-configured needles. While pain is subjective, it was surprising to note the patient population did not record appreciable increase in pain until the bend angle θ exceeded 30°–40°. The data suggest optimum design of a low pain needle for maximizing fluid collection rates is to provide a bend angle θ of about 30° and preferably between 20° and 40° with the tip 530" of the needle bent above the plane of the needle 510".

In certain applications (for example, collecting interstitial fluid for testing), it is desirable for the fluid to have a low blood content so as to be substantially blood-free. By substantially blood free, it is meant a sample with a hemocrit content of less than 10%. Using the bent needle 510" as described, the frequency of occurrence of blood in a sample increases compared to a straight needle, but the samples continue to be substantially blood free. The present needle 510" can also be used to collect higher blood content samples. In both, the design as described increases flow rate while retaining a low pain quality.

In addition to the bend angle described above, the needle 510 is dulled at the penetration end. The dulled edges at the penetration end have benefits separate from the displaced tip described above. Specifically, the dulled edges are found to reduce the amount of unwanted blood in a collected sample of interstitial fluid.

Figure 6:
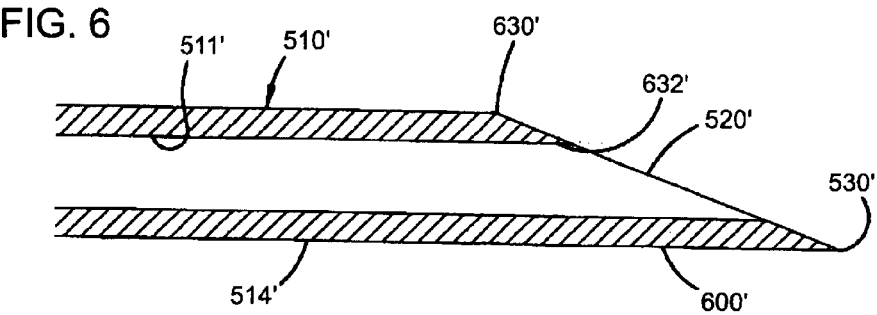
FIG. 6 is a side sectional view of a tip of a prior art needle.
Figure 7:
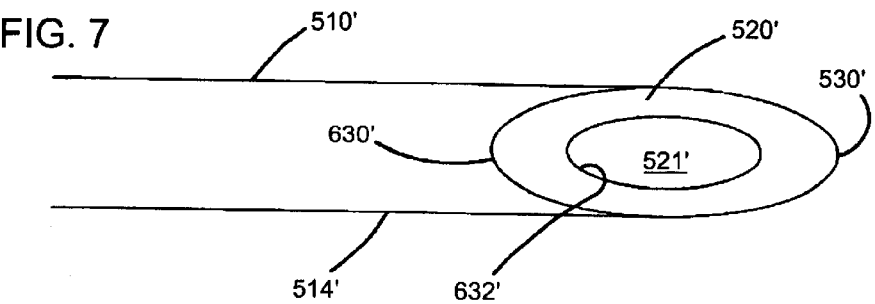
FIG. 7 is a top plan view of the needle tip shown in FIG. 6.
Figure 8:
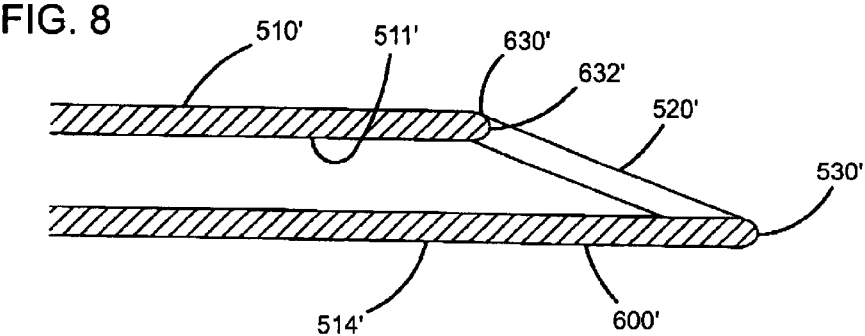
FIG. 8 is a side elevation view of the needle shown in FIGS. 6 and 7 following dulling of the needle tip.

FIGS. 6–8, illustrate a needle having a straight tip before and after its edges are dulled. Although the dulled edges are illustrated on a needle having a straight tip, they also could be used in conjunction with a displaced tip as described above. Elements and structures that are in common with the embodiments described above are marked with the same reference numerals with the addition of an apostrophe.

Referring now to FIGS. 6 and 7, the beveled face 520' is initially formed by grinding the needle 514' at the penetration end 600' as discussed above to form opening 521' (shown in FIG. 7). This grinding forms an outer peripheral edge 630', which is defined by the intersection of the beveled face 520' and the outer surface of the cylindrical body 514'. Additionally, an inner peripheral edge 632' is defined by the intersection of the beveled face 520' and the interior surface 511' of the needle body 514'. Upon grinding the needle to form the beveled face 520', the inner and outer peripheral edges 630' and 632' and tip 530' are initially sharp (i.e., are formed at substantially non-rounded intersections).

After the beveled face 520' is formed, the inner and outer edges 630' and 632' and tip 530' are dulled so that they become burnished or radiused. The dulled edges are formed in a burnishing operation by tumbling the needle 510' in a tumbler with a polishing medium. In one possible embodiment, the polishing medium is a fine media such as 1 mm ceramic spheres and a soap solution. About 5,000 needles are tumbled in a single batch in the polishing medium for about 20 minutes. Other possible tumbling methods use a different polishing medium, different batch sizes, or different lengths of time.

Referring to FIG. 8, this process dulls the inner and outer edges 630' and 632' and tip 530'. In one possible embodiment, the edges 630' and 632' and tip 530' are dulled to a radius of about 0.002 inch or about 0.05 mm. Although a burnishing process is described herein, manufacturing processes other than tumbling may be used to form the dulled edges.

From the foregoing detailed description, the present invention has been described in a preferred embodiment.

Modifications and equivalents of such disclosure are intended to be included in the appended claims. For example, the benefits of the displaced tip can be attained without the dulled edges of the needle. Similarly, the benefits of the dulled edges can be attained without the displaced tip of the needle. Additionally, all needles have been shown with a single bevel. Nevertheless, the present invention is applicable to a needle with multiple bevels.

The claim invention is:

1. An apparatus for collecting a body fluid for testing for an analyte contained within said body fluid, said apparatus comprising:
   a needle for penetrating a patient's skin to access said fluid within said skin;
   said needle having a hollow body extending from a first end to a second end with a fluid pathway extending between said ends, said hollow body having an exterior surface;
   said second end positioned to deposit fluid for subsequent testing; and
   said first end configured to penetrate said skin and comprising:
      a beveled face on a front side of said hollow body, said beveled face terminating at a penetration tip and having an opening in communication with said fluid pathway; and
      a bend within said beveled face wherein at least a portion of said beveled face is deflected whereby said penetration tip protrudes laterally beyond said exterior surface of said hollow body on said front side.

2. An apparatus according to claim 1 wherein said body is substantially tubular and said beveled face comprises a substantially flat surface.

3. An apparatus according to claim 1 wherein an interior surface of said body defines said fluid pathway, said apparatus further comprising:
   said beveled face intersecting with said exterior surface of said hollow body to define an outer peripheral edge and said beveled face intersecting with said interior surface to define an inner peripheral edge defining said opening;
   said outer peripheral edge having a dulled configuration.

4. An apparatus according to claim 3 wherein said inner peripheral edge has a dulled configuration.

5. An apparatus according to claim 1 wherein the needle is configured to penetrate into and not through the dermis.

6. An apparatus according to claim 1 wherein said hollow body defines a central axis and said first end forms an angle with said central axis between about 20° and 40°.

7. An apparatus according to claim 6 wherein said first end forms an angle with said central axis of about 30°.

8. An apparatus according to claim 1 wherein said beveled face is formed by a single grind.

9. An apparatus according to claim 1 wherein said beveled face is formed by multiple grinds.

10. A method for collecting a sample of body fluid from a skin layer of a patient, said method comprising:
    selecting a needle according to claim 1; and
    penetrating said tip into said skin layer to collect said body fluid within said hollow body.

* * * * *